(12) United States Patent
Maenosono et al.

(10) Patent No.: US 7,347,835 B2
(45) Date of Patent: Mar. 25, 2008

(54) PROCESS FOR PRODUCING PAD BASE FOR ENDERMISM, AND PAD BASE FOR ENDERMISM, AND INJECTION NEEDLE

(75) Inventors: Shinya Maenosono, Yokohama (JP); Yasushi Suzuki, Nakamarucho (JP); Hiroshi Akitomo, Hosoda (JP); Hidetoshi Hamamoto, Kitajima-cho (JP); Masaki Ishibashi, Naruto (JP)

(73) Assignee: Medrx Co., Ltd., Higashikagawa-Shi (JP)

( * ) Notice: Subject to any disclaimer, the term of this patent is extended or adjusted under 35 U.S.C. 154(b) by 0 days.

(21) Appl. No.: 10/560,085

(22) PCT Filed: Jun. 10, 2004

(86) PCT No.: PCT/JP2004/008514

§ 371 (c)(1),
(2), (4) Date: Dec. 9, 2005

(87) PCT Pub. No.: WO2004/108204

PCT Pub. Date: Dec. 16, 2004

(65) Prior Publication Data

US 2006/0163215 A1    Jul. 27, 2006

(30) Foreign Application Priority Data

Jun. 10, 2003   (JP) .............................. 2003-165250

(51) Int. Cl.
  *A61B 17/20*  (2006.01)
(52) U.S. Cl. ..................................... 604/46
(58) Field of Classification Search ............ 604/46–47, 604/264, 272; 264/204
See application file for complete search history.

(56) References Cited

U.S. PATENT DOCUMENTS

| | | | |
|---|---|---|---|
| 6,334,856 B1 | 1/2002 | Allen et al. | |
| 6,379,324 B1 | 4/2002 | Gartstein et al. | |
| 6,565,532 B1* | 5/2003 | Yuzhakov et al. | 604/142 |
| 6,623,457 B1* | 9/2003 | Rosenberg | 604/191 |
| 2002/0082543 A1* | 6/2002 | Park et al. | 604/21 |
| 2002/0193754 A1 | 12/2002 | Cho | |

(Continued)

FOREIGN PATENT DOCUMENTS

JP    53-92588    8/1978

(Continued)

*Primary Examiner*—Nicholas Lucchesi
*Assistant Examiner*—Theodore J Stigell
(74) *Attorney, Agent, or Firm*—Wenderoth, Lind & Ponack, L.L.P.

(57) ABSTRACT

The present invention provides a production process for obtaining a pad base for endermism capable of administering a drug in the skin without vibration. One side end of a thin metal wire is immersed in a solution containing a synthetic resin raw material in a lengthwise direction, the synthetic resin raw material solution adheres to a periphery of the thin metal wire, the synthetic resin raw material solution is hardened and then the thin metal wire is pulled out. The resulting minute needle is a hollow tubular body and the outer wall thereof is thickened toward the bottom. The minute needle is installed upright on the skin side of a patch base, and a drug in the hollow portion of the minute needle is injected in the skin and can be provided for endermism.

5 Claims, 3 Drawing Sheets

U.S. PATENT DOCUMENTS

| | | |
|---|---|---|
| 2004/0010237 A1 | 1/2004 | D'Ussel |
| 2004/0049150 A1 | 3/2004 | Dalton et al. |
| 2005/0137536 A1 | 6/2005 | Gonnelli |

FOREIGN PATENT DOCUMENTS

| | | |
|---|---|---|
| JP | 2003-501163 | 1/2003 |
| WO | 99/64580 | 12/1999 |
| WO | 02/07813 | 1/2002 |
| WO | 02/100474 | 12/2002 |

* cited by examiner

PROCESS FOR PRODUCING PAD BASE FOR ENDERMISM, AND PAD BASE FOR ENDERMISM, AND INJECTION NEEDLE

TECHNICAL FIELD

The present invention relates to a pad base for endermism used when percutaneously administering a drug which acts on organism in vivo, a process for producing the same, and an injection needle. The pad base is a portion assuming the percutaneous administration of a drug in a pad for percutaneous medication. The pad for percutaneous medication is an article covering the pad base with, for example, a pressure-sensitive adhesive sheet from the reverse of the skin side, and the like. When the pad for endermism is used, the pad base side is pasted on the skin.

BACKGROUND ART

The skin functions as a barrier for protecting the body and inhibits the invasion of a foreign substance in organism. Specifically, the stratum corneum of the outermost layer which is directly brought in contact with the foreign substance assumes the great role as a barrier. To be sure, although the digestive tract is the same as the skin from the viewpoint of being directly brought in contact with the foreign substance, the digestive tract has no barrier of stratum corneum such as the skin, and it is rather composed of the nutritional absorptive cell having function positively taking in nutritional components from the foreign substance, namely foods. Both the skin and the digestive tract differ from each other greatly in this point.

On the other hand, the skin also has a function (a function of insensible perspiration) of discharging, and can be considered not as a simple protective membrane but an organ having adjusting function of permeating substances.

By the way, intramuscular injection, oral administration and administration from the colon by a suppository have been known as the administration procedure of a drug to organism. A percutaneous absorption method of administering from the skin has been proposed focusing attention on the above-mentioned function of the skin. According to the percutaneous absorption method, the administration is nearly indolent, the control of medication is easy, adverse reaction is hardly generated, and it is expected that the QOL (Quality Of Life) of a subject is also remarkably improved because of the convenience of administration mode. Further, isosorbide dinitrate, estradiol, tulobuterol, nicotine, clonidine, scopolamine, fentanyl, lidocaine and the like in addition to nitroglycerine have been developed as percutaneously absorptive type pharmaceuticals.

The above-mentioned percutaneously absorptive type pharmaceuticals has advanced the study of percutaneous absorption of a drug and it has been clear that there were many drugs which could not be percutaneously absorbed by any method in accordance with the proceeding.

Then, a method of instantaneously perforating extremely fine pores in the skin and introducing a drug utilizing the procedure of Electroporation which is used for introducing gene in cells; a method of Iontophoresis which introduces into the skin an ionized drug using the technique of electrophoresis; or an administration method combining these have been devised as the percutaneous absorption method next generation instead of the procedure of simply diffusing and absorbing a drug from the stratum corneum into the skin in conventional methods.

As a means for perforating fine pores in the skin in like manner as the Electroporation, a MicroPatch method of bringing a pad with numerous tiny needles in contact with the skin and injecting a drug from the stinging needles site has been proposed.

To illustrate the MicroPatch method more specifically, a pad for endermism used in the MicroPatch method is equipped with a plural number of solid-core thick and short needles (made of silicon, a metal, or a plastic) with acicular pyramids of 10 to 50 μm and a reservoir for drug solution. When it is used, the above-mentioned needles sting the skin, gaps are broadened by vibrating the contact plane of the needles with the skin by a vibrator (100 MHz to 2000 MHz), and the drug solution from the above-mentioned reservoir is designed to be invaded into the skin from the extremely fine pore spots of the skin (for example, refer to U.S. Pat. No. 6,183,434).

As the drug administered by the MicroPatch method, insulin, morphine, α-interferon, parthyroid hormone, erythropoietin and the like are developed (Altea Therapeutics Inc., Atlanta, USA), insulin and the like have been already under the first phase of clinical test and studies for practical application are proceeding.

As the administration method, a non needle injection method which is in contrast to the above-mentioned method is also proposed. Concretely, a method of administering subcutaneously under pressuring an injection solution, or a method of using gas with high pressure by which the powder of a drug is subcutaneously beaten in under high pressure, or the like are proposed. Practically, a portion of them is already commercialized.

Although these administration methods have both merits and demerits, the MicroPatch method is a superior method from the viewpoints that it does not require specific devices and any one can easily use it.

DISCLOSURE OF THE INVENTION

As described above, since the MicroPatch method is a method of stinging the skin with a solid-core needle and injecting a drug from a gap between the needle and the skin, it is necessary to vibrate the spot at the injection by a vibrator; therefore electric power and the like are essential, and a more convenient procedure is desired.

Consequently, the present invention has been performed to overcome the above-mentioned circumstances, and the object of the present invention is to provide a pad base for endermism capable of administering a drug in the skin without vibration in the MicroPatch method. Further, the object is also to provide a production process capable of easily obtaining the pad base for endermism.

A thin needle is desired for mitigating pain in a usual injection needle, but when it is too thin, there is a fear of fracturing, and if it fractures, there is a fear that it remains in the skin and badly influences an organism.

Accordingly, in terms of the injection needle of the present invention, the object is to provide a needle which does not easily fracture.

The pad base for endermism of the present invention is characterized by a pad base containing a minute needle installed upright on the skin side of a patch base for skin, wherein the minute needle is in a hollow tubular structure and the outer wall thereof spreads and is thickened toward the patch base.

Since the minute needle itself is in a hollow tubular structure as described above, the above-mentioned minute needle stick in the skin when a pad for endermism having the pad base is pasted on the skin, therefore a drug in the minute needle is percutaneously administered by injecting a drug for administration (liquid drug and the like) in the hollow portion. Further, since the minute needle spreads and is thickened toward the bottom, it hardly fractures and there is little fear that it remains in the skin. Thus, according to the pad base for endermism of the present invention, a drug can be administered without carrying out operation that a gap is broadened by vibrating the contact face of the skin with the needle as conventionally carried out; therefore a vibrator, its electric power and the like are not required, and a drug can be more simply administered.

Further, the process of the present invention capable of producing the above-mentioned pad base for endermism is characterized in that one side end of a thin metal wire is immersed in a solution containing a synthetic resin raw material in a lengthwise direction, the synthetic resin raw material solution adheres to a periphery of the thin metal wire, the synthetic resin raw material solution of a is hardened, and the thin metal wire is pulled out to form a tubular minute needle. Further, it may be acceptable that there are a plurality of the thin metal wires in the steps, and a plurality of the minute needles are formed. The above-mentioned "hardening" includes a case that the solvent of the solution of a synthetic resin raw material is evaporated to precipitate a raw material resin component, a case that the liquid raw material resin component is reacted to be solidified, and the like.

The mechanism of obtaining the minute needle which spreads and is thickened toward the bottom is illustrated according to the above-mentioned method. For example, when a solution in which a synthetic resin is dissolved in a solvent in a low concentration is used as the synthetic resin raw material solution and the above-mentioned solvent is evaporated in condition in which one side end of the thin metal wire is immersed in a lengthwise direction, the liquid level of the raw material resin solution at a spot where the thin metal wire does not exist is gradually lowered and the raw material resin solution remains by adhering at the initial position of liquid level; therefore the minute needle is thickened toward the bottom for the above-mentioned lowered liquid level. The synthetic resin thus hardened by evaporation of a solvent forms a tubular body (minute needle) which is thickened toward the bottom, while a hole is formed by the portion of the thin metal wire.

Further, when a thermoplastic resin is used as the synthetic resin, one side end of the thin metal wire is immersed in the synthetic resin raw material solution which is a melted resin by heating, a mode that the liquid level of the solution of a synthetic resin raw material is raised at the portion of the thin metal wire is made, and it is hardened in such condition. Further, as a procedure for pasting the solution of a synthetic resin raw material as if it is raised around the thin metal wire, there are a method of deeply immersing a thin metal wire once in the synthetic resin raw material solution and then raising it; a method of vibrating the synthetic resin raw material solution in condition in which one side end of the thin metal wire is immersed and raising the solution on the surface of the thin metal wire with support; a method of appropriately adjusting the viscosity of the synthetic resin raw material solution and letting the solution rise up with support; and the like. When the thin metal wire is pulled out after hardening the resin, the portion of the thin metal wire becomes a hole and a tubular body (minute needle) which is thickened toward the bottom is formed.

The synthetic resin material in the solution of synthetic resin raw material includes a polypropylene, polyurethane, aramid, fluorine-containing polyimide and the like, and in particular, a biodegradable resin is preferable.

When the minute needle is made of a biodegradable resin, the minute needle made of the biodegradable resin is decomposed in organism, and there is little bad influence for organism, even if the edge of the minute needle and the like are notched and remains in the skin. When the minute needle is made of the biodegradable resin and the administering drug, the minute needle is decomposed in organism, and there is little bad influence for organism as stated above, even if the edge of the minute needle and the like are notched and remains in the skin. In addition, a drug is also administered by the minute needle itself dissolving (decomposing) in organism.

As the biodegradable resin, polylactic acid, polyethylene succinate, polybutylene succinate-adipate, polybutylene succinate-carbonate, polycaprolactone, polyester amide, polyester carbonate, polyvinyl alcohol, polyhydroxybutylate, mantriose, cellulose, cellulose acetate, collagen, and a mixture thereof are recommended. In particular, polylactic acid or copolymer of lactic acid with glycolic acid is preferable. For example, copolymer of lactic acid with glycolic acid, which has been already used as medical drugs, is gradually hydrolyzed in tissue to be lactic acid and gradually disappears.

Further, in case of a polylactic acid, a polylactic acid having a molecular weight of 100000 to 500000 is more preferable because an adhering amount to the above-mentioned thin metal wire is appropriate at the production process, the pulling-out performance of the above-mentioned thin metal wire after hardening is further better and the quality of the membrane (tubular body) completed is excellent.

As the solution of a synthetic resin raw material, a solution in which an administering drug is added in the biodegradable resin may be used.

Further, the injection needle of the present invention is characterized in that an outer wall of a needle portion of the injection needle spreads and is thickened toward a connection spot thereof with the syringe of the injection needle. Thus, since the outer wall of the needle portion spreads and is thickened toward the bottom, it hardly fractures and there is few fears of remaining in the skin.

BEST MODE FOR CARRYING OUT THE INVENTION

The pad base for endermism of the present invention and the production process thereof are specifically illustrated below referring the drawings showing examples, but the present invention is not limited to the examples illustrated. It can be also carried out by appropriately adding modifications within a range adaptable in the purport described above and later, and any of them is included in the technical scope of the present invention.

Firstly, one example of the process for producing the pad base for endermism of the present invention is illustrated.

As a solution of a synthetic resin raw material, for example, a solution in which a polylactic acid is dissolved in chloroform is prepared. The above-mentioned raw material solution is poured in a shallow vat made of a metal, one side ends of a plural number of the thin metal wires are immersed in the solution to a lengthwise direction, and the above-mentioned raw material solution is pasted on the peripheral surface of these thin metal wires. Chloroform as a solvent is removed by drying, the liquid level of the raw material solution is lowered thereby in condition in which the raw material solution adheres to the peripheral surface of the thin metal wires, and the polylactic acid is hardened. Then, the thin metal wires are pulled out from the polylactic acid hardened and taken out from a metal vat.

Figure 2:
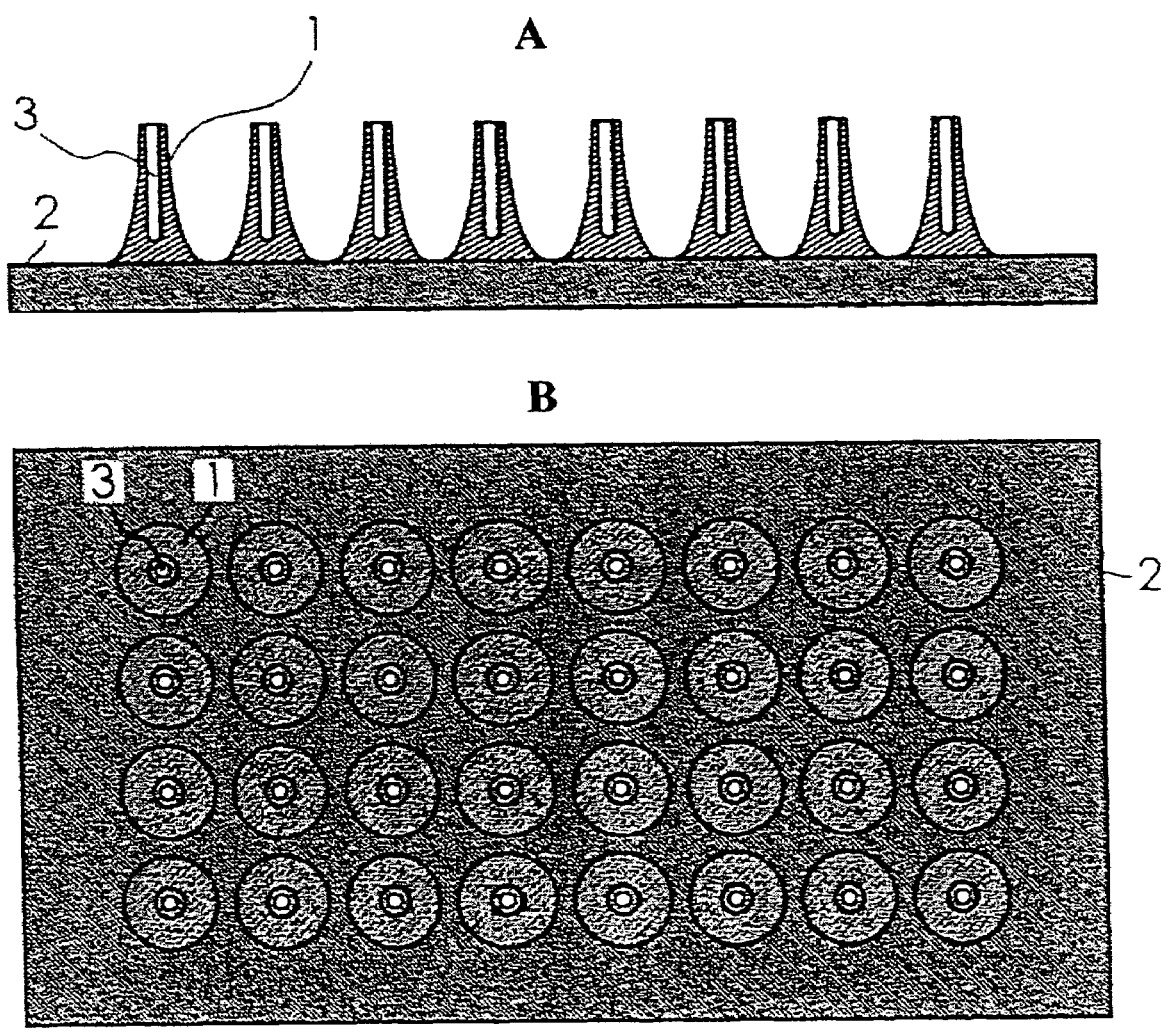
FIG. 2 is a view showing the pad base for endermism of an embodiment of the present invention.

In this way, the pad base for endermism which is shown in FIG. 2 (2A: a sectional view representing the pad base for endermism related to the one embodiment of the present invention, FIG. 2B: an upper view of the pad base) is obtained. The pad base obtained is a base in which many minute needles 1 are installed upright on the patch base 2, the minute needles 1 have a cylindrical member with a bottom whose skin face side was opened and its outer wall is thickened toward the bottom for the patch base 2. Further, the upper side in FIG. 2A is a patch face to the skin. In FIG. 2, it is illustrated as if the minute needles 1 and the patch base 2 are separately composed, but they are produced by integral molding as grasped from the above-mentioned production processes.

The pad base for endermism includes a pad covered with a pressure-sensitive adhesive sheet from the reverse of skin side (the lower side in FIG. 2A) of the above-mentioned pad base, and is used by pasting it on the skin by the pressure-sensitive adhesive sheet. Alternatively, a drug is occasionally administered from the hollow portion in a manner similar to the injection by compressing the needle to stick the skin without adhesive agent.

When it is used, a drug solution is preliminarily filled in the hollow portions 3 of the minute needles 1 by sucking the drug solution from a drug solution container and the pad for endermism equipped with the pad base is pasted on the skin. By applying pressure on the patch base 2, the minute needles 1 sting an organism, and the drug solution in the hollow portions 3 is injected in organism from the edges of the minute needles 1. The administered drug which is filled in the tubes (in the hollow portions 3) of the minute needles 1 may be any of liquid, cream, gel, suspension liquid or powder, and is not substantially limited excluding a drug not suitable for percutaneous administration.

Figure 1:
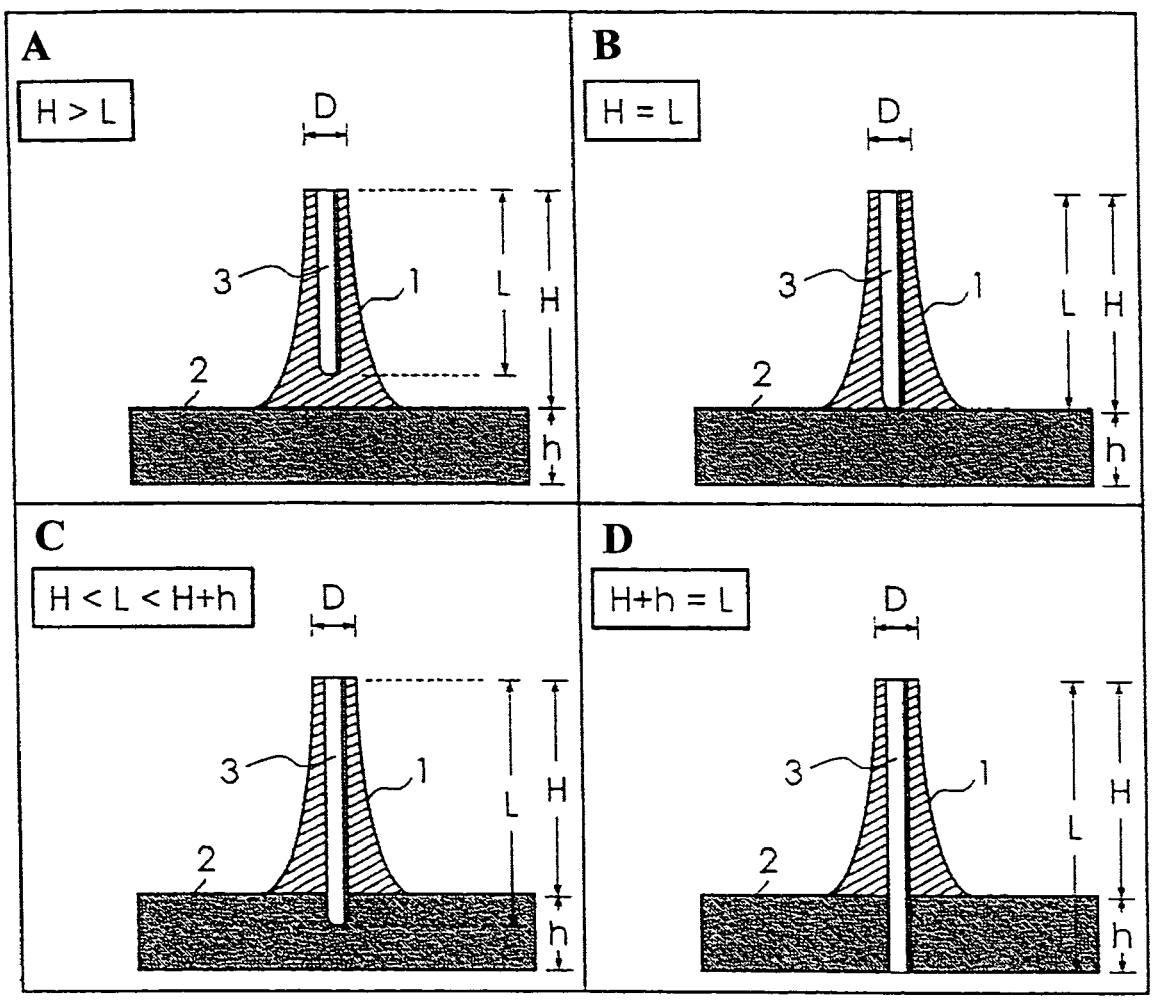
FIG. 1 is a sectional view for illustrating the shape of the hollow portion of the minute needle in the pad base for endermism of the present invention.

Further, the depth of the hollow portions 3 of the minute needles 1 may be deeper than those shown in FIG. 2. Concretely, as shown in FIG. 1B [sectional views for illustrating the form of the hollow portions of the minute needles], there may be those in which the height H of the minute needles 1 is the same as the depth L of the hollow portions 3 [H=L (wholly hollow type: TYPE 2)], those in which the hollow portion 3 reaches on way to the thickness h of the patch base 2 as shown in FIG. 1C [H<L<H+h (semi-penetration type: TYPE 3)], and those in which the hollow portion 3 penetrate the patch base 2 as shown in FIG. 1D [H+h=L (whole penetration type: TYPE 4)]. Further, as shown in FIG. 1A, those in FIG. 2 are one in which the depth L of the hollow portion 3 is shallower than the height H of the minute needles 1 [H>L (semi-hollow type: TYPE 1)]. It is hard to define a boundary clearly dividing the minute needles 1 and the supporting portion 2, in which the minute needles 1 and the patch base 2 were integrally molded, but here at curvature shall be deemed as infinite, that is, a planar portion shall be deemed as a boundary plane, a portion below the plane shall be deemed as the patch base 2 and a portion installed upright from this is called as the minute needles 1.

The depth of the hollow portion 3 of each of the minute needles 1 in the pad base equipped with a plural number of the minute needles 1 may be wholly the same, or those having different depths may be used in combination. Further, as shown in the above-mentioned TYPE 4 (FIG. 1D), when the hollow portions 3 penetrate the patch base 2 from the minute needles 1, a drug storing vessel is provided at the reverse of skin side of the patch base 2, and a drug may be fed to continuously carry out the administration of a drug.

In like manner as the above-mentioned description, as the injection needle related to one embodiment of the present invention, one side end of the thin metal wire may be immersed in the solution of a synthetic resin raw material to a lengthwise direction, the solution of a synthetic resin raw material adheres around the thin metal wire, the solution of a synthetic resin raw material is hardened and then the thin metal wire may be pulled out to form a tubular minute needle. The needle obtained in such a manner has the outer wall thickened toward the bottom.

According to the pad base for endermism of the present invention, since the minute needles are thickened toward the bottom, they hardly fracture; therefore there is little fear that they remain in the skin. Since a drug can be filled in the hollow portions of the minute needles 1, a drug can be administered in the skin without using a vibrator by stinging the minute needles injected with the drug in the skin, therefore it is simple.

Further, according to the process for producing the pad base for endermism of the present invention, the pad bases in which the tubular minute needles are installed upright from the patch base and the outer walls of the minute needles are thickened toward the bottom for the patch base can be easily prepared.

According to the injection needle of the present invention, the needle portion hardly fractures and there is little fear that they remain in the skin.

EXAMPLES

Examples 1 to 3

As a section bar for molding the minute needles, a section bar in which stainless steel wires (thin metal wires) having a length of about 30 mm and a diameter φ of 280 μm were vertically inserted by 5 wires in longitudinal and by 6 wires in a reticular pattern at an interval of 2 mm in a rubber plate was prepared. Then, the edges of stainless steel wires of the above-mentioned section bar were perpendicularly brought in contact with the bottom of a stainless steel dish, and 3 ml of a chloroform solution (the solution of a synthetic resin raw material) containing polylactic acid with a molecular weight of 101700 was poured in the stainless steel dish. After that these were left alone, chloroform was evaporated by naturally drying, the liquid level of the solution was lowered in condition in which the chloroform solution containing polylactic acid was pasted on the peripheral surface of stainless steel wires and the polylactic acid was solidified. Then, the stainless steel wires were taken out from the stainless steel dish to obtain a pad base for endermism. Further, solutions with 5, 6 and 7% by weight as the concentration of polylactic acid in the above-mentioned chloroform solution containing polylactic acid were prepared, and pad bases which were obtained for the respective solutions were referred to as Examples 1, 2 and 3.

Any of the above-mentioned Examples 1 to 3 was a pad base for endermism which had a plural number of the minute needles with a shape as shown in FIG. 1D.

Examples 4 to 6

A similar section bar of the minute needles as the above-mentioned Examples 1 to 3 was used and the edges of stainless steel wires of the above-mentioned section bar were perpendicularly brought in contact with the bottom of a stainless steel dish. 3 ml of a chloroform solution containing polylactic acid with a molecular weight of 67400 was poured in the stainless steel dish, left alone, and the polylactic acid was solidified by natural drying. Then, the stainless steel wires were taken out from the stainless steel dish to obtain a pad base for endermism. Further, solutions with 10, 11 and 12% by weight as the concentration of polylactic acid in the above-mentioned chloroform solution containing polylactic acid were prepared, and pad bases which were obtained for the respective solutions were referred to as Examples 4, 5 and 6.

Any of the above-mentioned Examples 4 to 6 was a pad base for endermism which had a plural number of the minute needles with a shape as shown in FIG. 1D.

Examples 7 to 9

A similar section bar of the minute needles as the above-mentioned Examples 1 to 3 was used and the edges of stainless steel wires of the section bar were perpendicularly brought in contact with the bottom of a stainless steel dish. 3 ml of a chloroform solution containing polylactic acid with a molecular weight of 258700 was poured in the stainless steel dish, left alone, and the polylactic acid was solidified by natural drying. Then, the stainless steel wires were taken out from the stainless steel dish to obtain a pad base for endermism. Further, solutions with 1, 2 and 3% by weight as the concentration of polylactic acid in the above-mentioned chloroform solution containing polylactic acid were prepared, and pad bases which were obtained for the respective solutions were referred to as Examples 7, 8 and 9.

Any of the above-mentioned Examples 7 to 9 was a pad base for endermism which had a plural number of the minute needles with a shape as shown in FIG. 1D.

Examples 10 to 12

A similar section bar of the minute needles as the above-mentioned Examples 1 to 3 was used and the edges of stainless steel wires of the above-mentioned section bar were arranged so as to perpendicularly stand against the bottom while providing a little space from the bottom face of a stainless steel dish. To a chloroform solution containing polylactic acid with a molecular weight of 101700 (high molecular weight PLA) was added polylactic acid with a molecular weight of 10000 (low molecular weight PLA) in an amount of 0.1 part by weight based on the above-mentioned high molecular weight PLA, 3 ml of the mix solution was poured in the above-mentioned stainless steel dish, left alone so that one side ends of the stainless steel wires were immersed, and the polylactic acid was solidified by natural drying. Then, the stainless steel wires were taken out from the stainless steel dish to obtain a pad base for endermism. Further, solutions with 5, 6 and 7% by weight as the concentration of polylactic acid in the chloroform solution of the above-mentioned high molecular weight PLA were prepared, and pad bases which were obtained for the respective solutions were referred to as Examples 10, 11 and 12.

Figure 3:
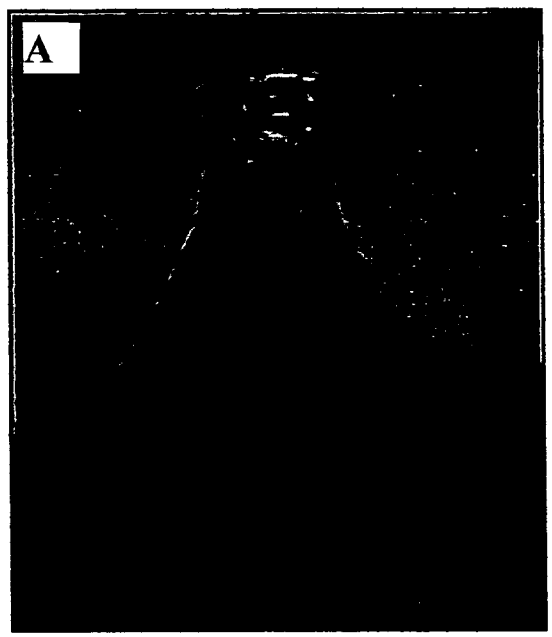
FIG. 3A is the microscopic photograph of the minute needle in the pad base for endermism of Example 10.
FIG. 3B is a schematic view thereof.
Figure 3:
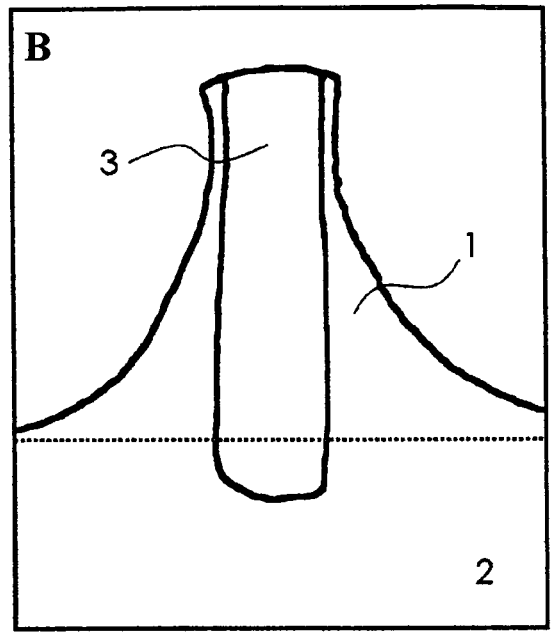

Any of the above-mentioned Examples 10 to 12 was a pad base for endermism which had a plural number of the minute needles with a shape as shown in FIG. 1C. The microscopic photograph (a magnification constant of 40-fold) of the minute needle in Example 10 obtained is shown in FIG. 3A. Further, its schematic view is shown in FIG. 3B.

Examples 13 to 15

A similar section bar of the minute needles as the above-mentioned Examples 1 to 3 was used, and the edges of stainless steel wires of the above-mentioned section bar were arranged so as to perpendicularly stand while providing a gap against the bottom of a stainless steel dish. Polylactic acid with a molecular weight of 10000 (low molecular weight PLA) in an amount of 0.1 part by weight based on the above-mentioned high molecular weight PLA was added to a chloroform solution containing polylactic acid with a molecular weight of 67400 (high molecular weight PLA), 3 ml of the mix solution was injected in the above-mentioned stainless steel dish, one side ends of the stainless steel wires were immersed in the solution, and the solution was raised on the surface of the stainless steel wires, left alone, and the polylactic acid was solidified by natural drying. Then, the stainless steel wires were drawn out and taken out from the stainless steel dish to obtain a pad base for endermism. Further, solutions with 10, 11 and 12% by weight as the concentration of polylactic acid in the chloroform solution of the above-mentioned high molecular weight PLA were prepared, and pad bases which were obtained for the respective solutions were referred to as Examples 13, 14 and 15.

Any of the above-mentioned Examples 13 to 15 was a pad base for endermism which had a plural number of the minute needles with a shape as shown in FIG. 1C.

Examples 16 to 18

A similar section bar of the minute needles as the above-mentioned Examples 1 to 3 was used, and the edges of stainless steel wires of the above-mentioned section bar were arranged so as to perpendicularly stand while providing a gap against the bottom of a stainless steel dish. To a chloroform solution containing polylactic acid with a molecular weight of 258700 (high molecular weight PLA) was added polylactic acid with a molecular weight of 10000 (low molecular weight PLA) in an amount of 0.1 part by weight based on the above-mentioned high molecular weight PLA, 3 ml of the mix solution was injected in the above-mentioned stainless steel dish, one side ends of the stainless steel wires were immersed in the solution, the solution was raised on the surface of the stainless steel wires, left alone, and the polylactic acid was solidified by natural drying. Then, the stainless steel wires were drawn out and taken out from the stainless steel dish to obtain a pad base for endermism. Further, solutions with 1, 2 and 3% by weight as the concentration of polylactic acid in the chloroform solution of the above-mentioned high molecular weight PLA were prepared, and pad bases which were obtained for the respective solutions were referred to as Examples 16, 17 and 18.

Any of the above-mentioned Examples 16 to 18 was a pad base for endermism which had a plural number of the minute needles with a shape as shown in FIG. 1C.

Further, the results of Examples 1 to 9 were shown in Table 1 and the results of Examples 10 to 18 were collectively shown in Table 2. Furthermore, respective evaluation with respect to the adhering performance of the chloroform solution containing polylactic acid (the solution of a synthetic resin raw material) to the stainless steel wires (thin metal wires) and the easiness of pulling-out of the stainless steel wires after hardening of polylactic acid are described.

TABLE 1

|  | Molecular weight of PLA | Concentration of PLA (% by weight) | Adhering amount of PLA to thin metal wire and membrane quality | Easiness of pulling-out of thin metal wire |
|---|---|---|---|---|
| Example 1 | 101,700 | 5 | Δ | Δ |
| Example 2 | 101,700 | 6 | ○ | ○ |
| Example 3 | 101,700 | 7 | ○ | ○ |
| Example 4 | 67,400 | 10 | X | X |
| Example 5 | 67,400 | 11 | X | X |
| Example 6 | 67,400 | 12 | X | X |
| Example 7 | 258,700 | 1 | Δ | X |
| Example 8 | 258,700 | 2 | Δ | X |
| Example 9 | 258,700 | 3 | Δ | X |

○: Better
Δ: Good
X: Slightly bad

TABLE 2

|  | Molecular weight of high molecular weight PLA | Concentration of high molecular weight PLA (% by weight) | Adhering amount of PLA to thin metal wire and membrane quality | Easiness of pulling-out of thin metal wire |
|---|---|---|---|---|
| Example 10 | 101,700 | 5 | Δ | ○ |
| Example 11 | 101,700 | 6 | ○ | ◎ |
| Example 12 | 101,700 | 7 | ○ | ◎ |
| Example 13 | 67,400 | 10 | X | X |
| Example 14 | 67,400 | 11 | X | X |
| Example 15 | 67,400 | 12 | X | X |
| Example 16 | 258,700 | 1 | Δ | X |
| Example 17 | 258,700 | 2 | Δ | X |
| Example 18 | 258,700 | 3 | Δ | X |

◎: Extremely better
○: Better
Δ: Good
X: Slightly bad

As mentioned above, the pad bases for endermism having the minute needles shown in FIG. 1C and FIG. 1D are obtained in Examples 1 to 18. Further, since either of the pad bases (the patch bases and the minute needles) of the above-mentioned Examples 1 to 18 is composed of polylactic acid, even if the minute needles fracture at usage and remain in the skin, they are anticipated to be biodegraded.

As grasped from the above-mentioned Tables 1 and 2, Examples 1 to 3 and 10 to 12 are more preferable among the above-mentioned respective Examples from the viewpoints of the adhering amount of polylactic acid to the stainless steel wires, the quality of membrane, and the easiness of pulling-out of the stainless steel wires.

The invention claimed is:

1. A process for producing a pad base for endermism comprising:
    dissolving a synthetic resin raw material in a solvent to form a synthetic resin raw material solution;
    immersing one side end of a thin metal wire in the synthetic resin raw material solution in a lengthwise direction to adhere the synthetic resin raw material solution to a periphery of the thin metal wire;
    hardening the synthetic resin raw material solution adhered to the thin metal wire in a shape spreading toward the one side end of the thin metal wire by evaporating the solvent to lower a liquid level of the synthetic resin raw material solution;
    pulling out the thin metal wire to form a tubular minute needle having a hollow portion; and
    installing said tubular minute needle upright on a skin side of a patch base for skin, to produce a pad base for endermism.

2. The process for producing a pad base for endermism according to claim 1, wherein the tubular minute needle is made of a biodegradable resin, or a biodegradable resin and an administering drug.

3. The process for producing a pad base for endermism according to claim 2, wherein the biodegradable resin is polylactic acid, or a copolymer of lactic acid and glycolic acid.

4. The process for producing a pad base for endermism according to claim 1, further comprising adjusting the depth of the hollow portion in the tubular minute needle, by
    bringing the one side end of the thin metal wire into contact with a bottom of a dish storing the synthetic resin raw material solution during immersion, thus resulting in the hollow portion in the tubular minute needle penetrating the patch base, or by
    providing a distance between the bottom of a dish storing the synthetic resin raw material solution and the one side end of the thin metal wire during immersion.

5. The process of producing a pad base for endermism according to claim 1, wherein a plurality of tubular minute needles are formed into a reticular pattern by arranging a plurality of thin metal wires prior to immersion in the synthetic resin raw material solution.

* * * * *